(12) United States Patent
Howell et al.

(10) Patent No.: US 7,505,857 B2
(45) Date of Patent: Mar. 17, 2009

(54) WATER QUALITY MONITORING DEVICE AND METHOD

(75) Inventors: Jason W. Howell, Maple Valley, WA (US); N. Eric Knudsen, Maple Valley, WA (US); Julia M. Howell, Maple Valley, WA (US); Renee L. Knudsen, Maple Valley, WA (US); Chris G. Bennett, Bothell, WA (US)

(73) Assignee: H2Observe, LLC, Maple Valley, WA (US)

( * ) Notice: Subject to any disclaimer, the term of this patent is extended or adjusted under 35 U.S.C. 154(b) by 0 days.

(21) Appl. No.: 11/466,378

(22) Filed: Aug. 22, 2006

(65) Prior Publication Data
US 2008/0052012 A1    Feb. 28, 2008

(51) Int. Cl.
*G01R 25/00* (2006.01)
*B01D 15/00* (2006.01)

(52) U.S. Cl. .......................................... 702/65; 210/85
(58) Field of Classification Search ............. 702/62–66, 702/22, 30–31; 210/85, 96.2, 634, 638, 660, 210/141
See application file for complete search history.

(56) References Cited

U.S. PATENT DOCUMENTS

| | | | |
|---|---|---|---|
| 4,849,098 | A | 7/1989 | Wilcock et al. |
| 5,527,470 | A | 6/1996 | Suda |
| 5,580,444 | A | 12/1996 | Burrows |
| 5,581,189 | A | 12/1996 | Brenn |
| 5,990,684 | A | 11/1999 | Merrill |
| 6,398,930 | B2 | 6/2002 | Fukunaga et al. |
| 6,444,172 | B2 | 9/2002 | Fukunaga et al. |

(Continued)

FOREIGN PATENT DOCUMENTS

EP    0672448 B1    9/1995

(Continued)

OTHER PUBLICATIONS

Globalspec; The Engineering Search Engine: Model 2200 PCX Particle Counter from Hatch Company, http://www.globalspec.com/FeaturedProducts/Detail/Hach/Model_2200_PCX_Particle_Co..., download date of Mar. 22, 2007.

*Primary Examiner*—John e. Barlow, Jr.
*Assistant Examiner*—Hien X Vo
(74) *Attorney, Agent, or Firm*—Seed IP Law Group PLLC (57) ABSTRACT

A device repeatedly measures a characteristic, such as electrical conductivity, of water in a water line. A plurality of the measurements are averaged to arrive at a water quality value. This value is displayed and another plurality of measurements are averaged to arrive at another value, which is then displayed in place of the previous value. The process continues at selected intervals in order to provide a continuous display of the condition of water in the line. Each new value is compared to a reference value representing a maximum acceptable level of contaminants. If the water quality value exceeds the reference value, an overvalue signal is produced, indicating an unacceptable level of contaminants in the water. The repeated measurements are obtained at selected intervals, and a new water quality value may be derived at the same intervals by discarding the oldest of the measurements from the previous plurality and including the most recent measurement to create a new plurality of measurements.

33 Claims, 3 Drawing Sheets

U.S. PATENT DOCUMENTS

| | | |
|---|---|---|
| 6,529,841 B2 | 3/2003 | Cocking et al. |
| 6,690,172 B2 | 2/2004 | Higo |
| 6,831,470 B2 | 12/2004 | Xie et al. |
| 2007/0090059 A1 | 4/2007 | Plummer et al. |

FOREIGN PATENT DOCUMENTS

| | | |
|---|---|---|
| GB | 2334575 A | 8/1999 |
| KR | 1020050005827 A | 1/2005 |

WATER QUALITY MONITORING DEVICE AND METHOD

BACKGROUND OF THE INVENTION

1. Field of the Invention

The present disclosure relates generally to the field of monitoring water in water lines, and in particular, to monitoring residential water supplies to measure dissolved solids.

2. Description of the Related Art

Availability of water is perhaps the most essential factor in determining where humans can live, raise food, and develop industry. Considerable resources are spent finding, moving, storing, and purifying water for human consumption. At the same time, water contamination is a large and growing problem. Point sources, such as sewage systems, feed lots, and industrial waste discharge, combines with non-point sources, such as cropland runoff from fertilizers and insecticides, highway runoff of oil and other automotive products, and atmospheric pollution captured by rain water, to raise the level of contaminants in the water that we rely on. This is in addition to natural mineral contaminants that are collected by water in rivers and aquifers.

Most water contaminants are carried as dissolved solids in the water. Generally, water purity is classified in relation to the total dissolved solids (TDS) in the water, and is measured in parts-per-million (ppm), by weight. In any given water sample there will be a combination of many contaminants, natural and man-made, that make up the TDS value of the sample. While concentrations of particular contaminants can be harmful at relatively low levels, as a rule, potability is classified in accordance with the TDS value of a water sample. The U.S. Environmental Protection Agency guidelines establish 500 ppm as a maximum acceptable level of TDS for drinking (potable) water. Levels above around 300 ppm usually affect the appearance or taste of water. Average tap water in the U.S. ranges between 140 and 400 ppm, with hard water above around 170 ppm. Commercial carbon/particulate filters can produce water in a range of around 50-150 ppm, while water below 50 ppm can be produced by reverse-osmosis filters, distillation, de-ionization, micro-filtration, etc. Extremely pure water below around 25-30 ppm is corrosive to some materials.

Notwithstanding the growing problems and concerns surrounding the question of water purity and availability, most of the water provided in the U.S. for domestic use is well within the standards established, and is safe for use. However, despite this fact, and the fact that most municipal treatment facilities operate to standards that far exceed the minimum standards set federally, most consumers have some level of concern for the quality of their own tap water. These concerns are fueled by news of intentional and accidental spills infiltrating the water supply, and by the aggressive advertising of the growing bottled and filtered water industry. As a result, many people routinely filter their tap water or buy bottled water.

The cost of filtering tap water is generally between three and twenty cents per gallon, while bottled water usually costs more than a $1 per gallon, and can be as high as $4 per gallon. Yet many people are unwilling to trust that their tap water will always be safe, and prefer, instead, to pay a premium for a real or perceived reliable source of clean water.

BRIEF SUMMARY OF THE INVENTION

According to an embodiment of the invention, a method is provided in which a characteristic, such as electrical conductivity, of water in a water line is repeatedly measured, and a plurality of the measurements are averaged to arrive at a water quality value. This value is displayed and another plurality of measurements are averaged to arrive at a new water quality value, which is then displayed in place of the previous value. The process continues at selected intervals in order to provide a continuous display of the condition of water in the water line.

Each time a new water quality value is produced it is compared to a reference value representing a maximum acceptable level of contaminants in the water. If the water quality value exceeds the reference value, an overvalue signal is produced, indicating an unacceptable level of contaminants in the water.

The repeated measurements are obtained at selected intervals, and a new water quality value may be derived at the same intervals by discarding the oldest of the measurements from the previous plurality of measurements and including the most recent measurement to create a new plurality of measurements, which is then averaged as before.

According to another embodiment, a device is provided that is configured to be coupled to a water line such that a pair of electrodes of the device is positioned in a stream of water flowing within the water line. The device is further configured to induce an electrical current in water passing between the electrodes and measure the current to obtain a conductivity reading of the water, and to repeat the process at selected intervals. The device is configured to use a plurality of readings to derive a water quality value, which is displayed on a face of the device, and which is periodically updated. The value is also compared with a reference value to detect changes in water quality, and in particular, to detect increases in total dissolved solids in the water.

DETAILED DESCRIPTION OF THE INVENTION

Figure 1:
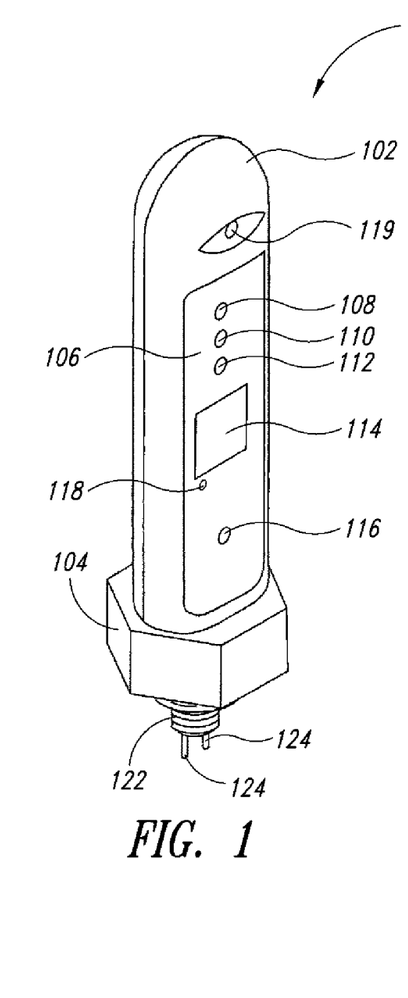
FIG. 1 is a front perspective view of a water quality monitor device according to an embodiment of the invention.
Figure 2:
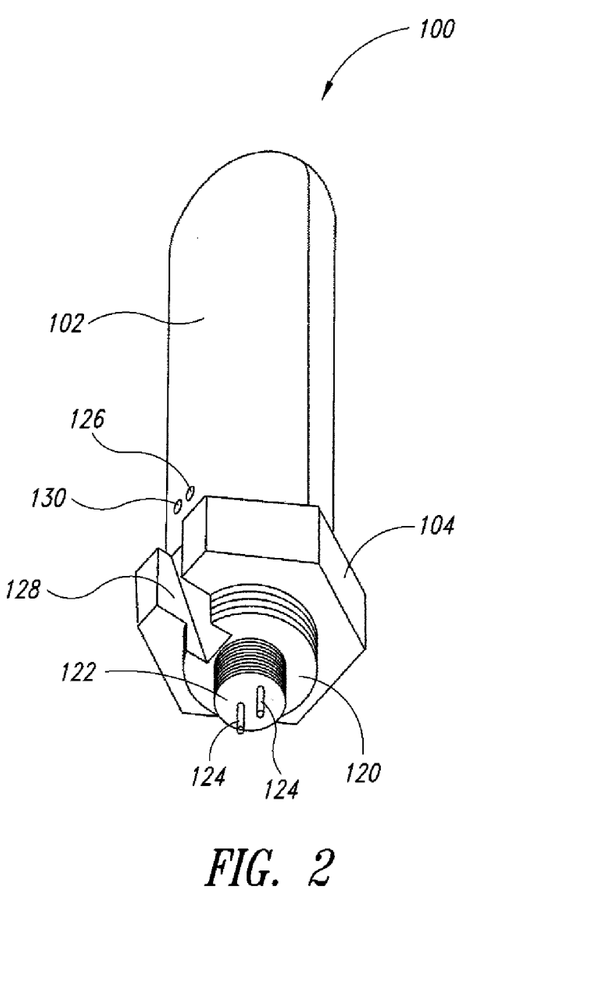
FIG. 2 is a rear perspective view of the water quality monitor device of FIG. 1.

FIGS. 1 and 2 illustrate a water quality monitor device 100 according to an embodiment of the invention. The device includes a body 102 and a base 104. A face panel 106 on a front surface of the body 102 provides access to many of the features of the device 100.

The face panel 106 includes a power button 108, a mode button 110, and a set button 112. A display panel 114, such as, for example, an LCD display, provides information related to user-selected options and water quality measurements. An audio alarm is provided within the body 102, positioned adjacent to an audio output aperture 116. A small reset aperture 118 provides access to a recessed reset button. A status light 119 provides basic operational information.

On a back surface of the body, a power socket 130 is configured to receive a connector from a power cable, while a relay control socket 126 is configured to receive a cable coupling the device 100 to a water shut-off relay.

The water quality monitor device 100 of the embodiment illustrated in FIGS. 1 and 2 is configured to be mounted on a sink, as will be described in more detail with respect to FIG. 3. Accordingly, the device 100 is provided with a threaded sink mount 120 extending from the base 104 and configured to be positioned in an aperture formed in the surface of a sink near the faucet. A pipe-threaded water line connector 122 extends below the sink mount 120, and a pair of test electrodes 124 extend from the water line connector 122. A cable bypass channel 128 is formed in a back portion of the base 104 and sink mount 120. The cable bypass channel 128 provides a passage through which the power and relay control cables can pass from beneath the sink surface to couple to their respective sockets 130, 126 in the back of the device 100. Alternatively, sockets or other connection ports are provided for direct access from beneath the sink mount. The monitor device 100 is configured to be mounted such that the electrodes 124 extend into the flow of water in a water line. In operation, the device places a voltage differential across the electrodes 124, thereby causing an electric current to flow in the water between the electrodes 124. The device is configured to measure the flow of electric current and correlate the resulting value with a corresponding level of total dissolved solids (TDS) in the water. This value is displayed in the display panel 114, and updated as the value changes. If TDS rises above a selected threshold, the device 100 is configured to provide an audible alarm, and to provide a shutoff signal for a water-control valve, as will be described below.

It is well known that a reliable indicator of the potability of water is the total dissolved solids present in the water. As the level of TDS increases, the suitability of the water for drinking decreases. It is further recognized that there is a high correlation between TDS in water and conductivity. It is possible, therefore, to obtain a relatively accurate measure of the potability of a water sample by measuring the conductivity thereof. The inventors have recognized that it is not necessary to determine specifically what contaminants are present in water in order to determine whether it is fit for drinking. Thus, a nonspecific test such as a conductivity test, which is inexpensive and repeatable, will serve to produce data that a consumer can use to decide whether it is necessary or justified to filter tap water or replace it with bottled water. The inventors have devised the water quality monitor configured to repeatedly perform water conductivity tests at selected intervals to monitor water quality in a location such as, for example, a residence.

Figure 3:
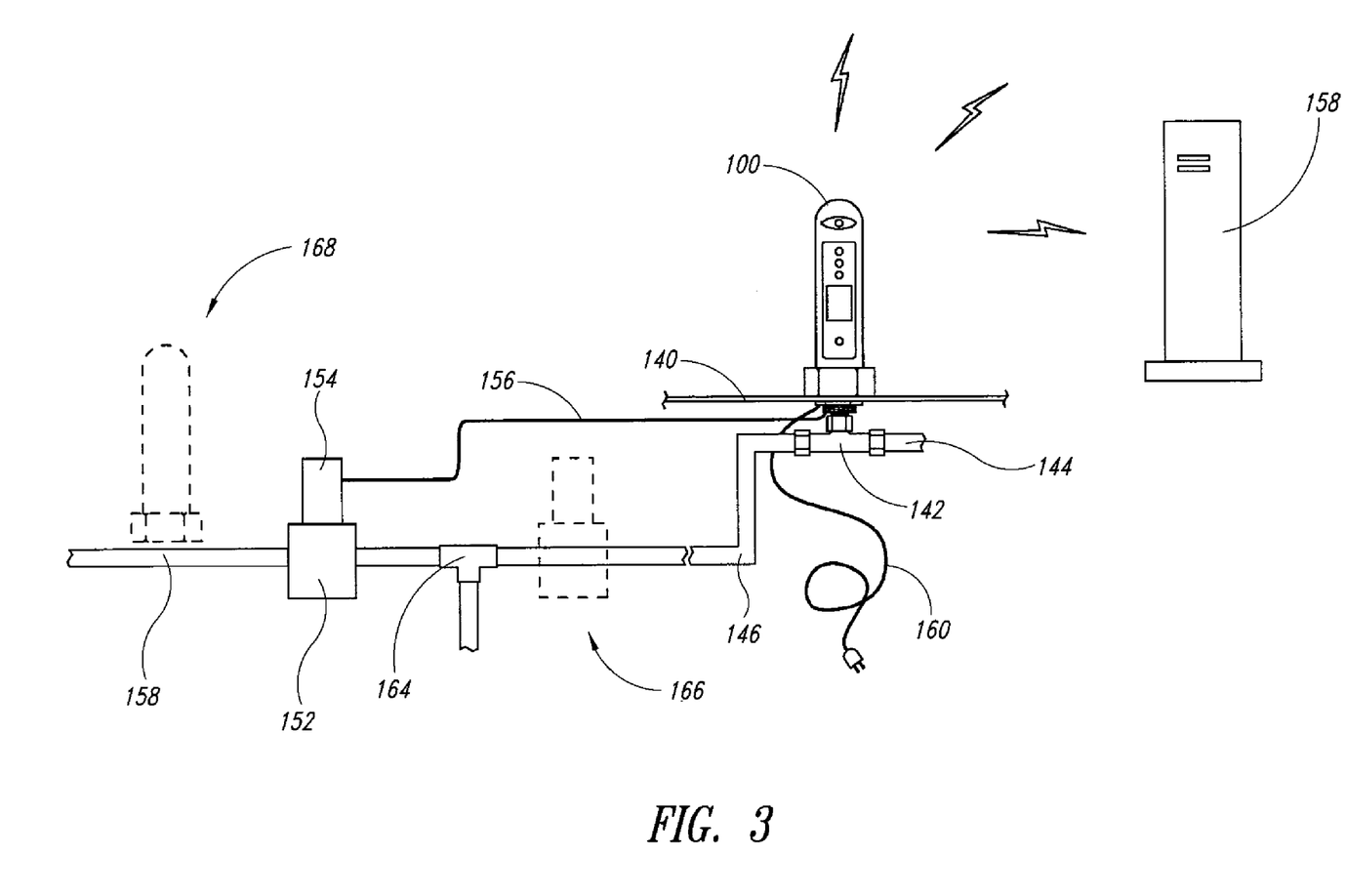
FIG. 3 illustrates a system for monitoring water quality according to an embodiment of the invention.

Referring now to FIG. 3, a monitoring system 150 according to an embodiment incorporating the water quality monitor device 100 of FIGS. 1 and 2 is described. The monitoring system 150 will be described with reference to a residential application. However, it will be recognized that the system may be employed anywhere water quality is a concern. In particular, businesses that require potable water can benefit from such a system. These may include, for example, restaurants, food processors, bottling companies, etc. Accordingly, the scope of the invention extends to include such applications, as well.

The monitoring device 100 is mounted to an upper surface of a sink 140 with the water line connector 122 extending below the sink 140. A tee junction 142 is threaded onto the water line connector 122 such that the electrodes 124 extend into the stream of water flowing through the junction 142. A water supply line 146 (usually the cold water supply line) is connected to one end of the tee junction 142, and a continuation 144 of the water supply line 146 extends between the tee junction 142 and the faucet of the sink 140.

An optional shut-off valve 152 may be positioned between a feeder line 158 from the municipal water main and a first branch 164 of the water line within the residence. A valve relay 154 is electrically coupled to the shut-off valve 152 to control operation of the valve. The relay 154 is coupled, via a relay control cable, 156, to the water quality monitor device 100. The relay control cable 156 traverses the cable bypass channel 128 to access the relay control socket 126 of the device 100.

A power cable 160 also traverses the bypass channel 128 to provide power to the device 100 from a power source below the sink. Most kitchen sinks include access to electrical power beneath the sink to provide power for dishwashing machines and waste disposal units. Accordingly, the power cable 160 for the monitoring device 100 is easily connected to power, either via a standard power outlet or by direct wiring.

The water quality monitor device 100 is configured to repeatedly monitor the TDS of water passing between the electrodes 124. In the event the level of solids in the water rises above the selected threshold, the device sounds an audible alarm and signals the relay 154 to energize the valve 152 to shut off the water. Thus, the user can use water directly from the municipal supply with confidence that the water does not contain TDS above the selected threshold.

According to an alternate configuration to that described above, the shut-off valve 152 may be positioned downstream from the branches that supply water to outside hose bibs, irrigation, and even laundry and bathrooms, as indicated in dashed lines at 166 in FIG. 3. In this arrangement only drinking water is shut off when the valve 152 closes. Such a configuration allows a residence to continue using water for non-potable applications even when incoming water is not suitable for drinking.

According to another configuration, as shown in dashed lines at 168, the monitor device 100 may be positioned upstream from the shut-off valve 152, and provision made to permit water to continue to flow past the monitor device 100, such as by shutting off drinking water, only, so that when the incoming water is again safe to drink, the device 100 will detect the drop in TDS and re-open the valve 152.

The water quality monitor 100 of FIGS. 1-3 has been illustrated and described for use on a sink or counter top. In this location, a user has easy access to the device to confirm that the device is operative and to note the water quality level, as indicated on the display panel 114, at any time. However, it will be recognized that the device 100 may be installed on a water line at any convenient location, and that it is not essential that the device 100 be instantly accessible.

According to an alternative embodiment, a monitor is provided that is configured to be positioned elsewhere along an incoming waterline. For example, the monitor may be coupled to a tee junction provided at the feeder line of the residence in a location such as a garage or crawl space. Furthermore, the monitor may be configured to include remote location of control and display functions such that a user can review and control operation of the device without actually going to where the device is positioned. For example, a wall mounted panel may be provided for this purpose. Alternatively, appropriate software and hardware modules can be provided such that the user can control and check the monitoring device from a computer. Such alternate configurations are within the abilities of one of ordinary skill, and fall within the scope of the invention.

While the monitor device of the embodiment described with reference to FIGS. 1 and 2 provides an overvalue alarm when TDS exceeds a single selected threshold, the device obtains continuous readings of the actual level of TDS. So, for example, if a transitory rise in TDS occurs that does not reach the threshold, it will go unnoticed, unless a user is actually watching the display panel at the time. Accordingly, embodiments are provided in which data collected by the monitor device 100 is stored in an internal memory for later retrieval, or transmitted to a storage device 158 such as a computer or other memory. In the embodiment illustrated in FIG. 3, the data is transmitted wirelessly to a nearby computer 158. Alternatively, the data may be transmitted via wired connection or other transmission means.

By storing the data obtained, a user can track changes in water quality over time, in order to obtain a long-term water quality image. Data from the continually operating device is stored for later review. Thus, a user can note conditions that would otherwise be ignored. For example, the water at a given location may be constantly high in TDS, though below the threshold; or there may be frequent spikes in TDS that approach but don't reach the threshold. In another case, the water quality may vary by season, or after heavy rain. These or other conditions may prompt the user to adjust the threshold of the device or take steps to obtain filtered water at particular times.

According to an embodiment of the invention, the data is transmitted from the monitor device to a central collection facility, where it is compiled with similar data from other residences and businesses around a given region. For example, the local storage device may be programmed to periodically transmit data via an internet connection, or some other transmission link. Alternatively, the monitor device itself may be configured to transmit data to a collection network. ZigBee™ is one example of a protocol that is known in the art and that may be employed for this purpose.

Centrally collecting such data allows municipal authorities to track sources of contamination and predict upcoming problems based on historic trends. Limited financial resources for upgrading water supply systems can then be allocated in a way that provides maximum benefit. National governmental agencies can use the data to locate or track particular contamination problems and evaluate progress of treatment programs. There will still be a need for on-site water testing for evaluation of specific contaminants or events, but, in accordance with the principles of the invention, first order tracking can be done more economically and more comprehensively than is currently possible.

Additionally, there are commercial benefits to collection of such data locally and nationally. For example, the provision of clean water can be a significant expense to a food processing company, especially if the water must be retreated in the plant before use. Thus, data that can show water quality trends geographically and over time can be very useful when a location is being sought for a processing facility. Such data may also be of use to companies that provide products designed to address water quality issues in homes or businesses, by allowing them to target specific areas that have a higher need of their products.

Figure 4:
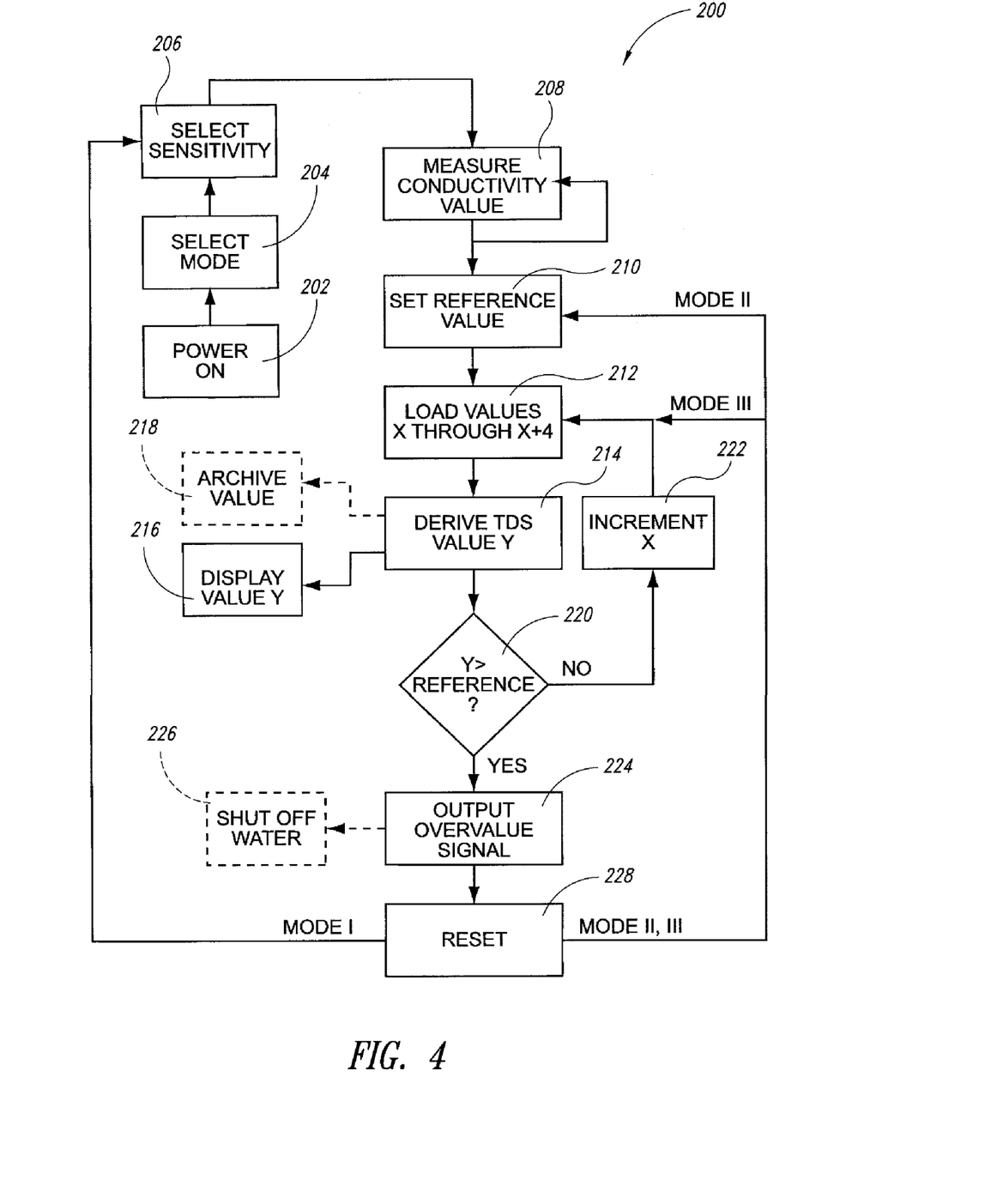
FIG. 4 is a flow chart illustrating a method for monitoring water quality in accordance with an embodiment of the invention.

Referring now to FIG. 4, a flow chart 200 is provided, which outlines operation of a water quality monitor according to an embodiment of the invention. Following a review of the steps outlined in FIG. 4, the operation will be described in more detail in relation to the monitor device 100 of FIGS. 1-3. It will be recognized that other monitor devices can also be configured to operate in accordance with the operation outlined here.

The process begins at step 202 with turning on the power to the monitor. In one embodiment, the user then selects a mode of operation for the device, step 204. A level of sensitivity is selected by the user in step 206. At this point, the monitor begins performing conductivity tests, or readings, at timed intervals (step 208), such as, for example, one second intervals, and repeats the tests continuously until the system is powered down or reset. Depending on the mode selected, the system may set a system reference value at step 210. At 212, the system obtains the measured conductivity values of five consecutive readings obtained in the measurement step 208. The value X of step 212 refers to the number, in a continuous sequence of measurements, of the first of five consecutive readings. At step 214, an average of five readings is obtained, which is correlated with the TDS corresponding to that value of conductivity to produce a TDS value Y. The value Y of TDS is then displayed at panel 114 of the device (216). Optionally, at step 218, the system transmits the value Y to a storage medium or remote storage facility.

Simultaneously with the display step 216, the TDS value Y is compared, in step 220, with the reference value previously established. If the value Y does not exceed the reference value (the NO path), the value of X is incremented at 222, and the system returns to step 212. By incrementing X, the first of the original five measured conductivity values is discarded, and a new fifth value is obtained for the averaging step 214. This is sometimes referred to as a moving window sampling method.

If the value Y exceeds the reference value at step 220, the system outputs an overvalue signal at step 224. This signal may include an audible alarm, flashing of a status light, or any other appropriate signal. At this point, the system may optionally control a water valve to close, at step 226. When the overvalue signal is produced, the user must either reset the system, step 228, or power down the system. A reset will restart operation of the system at one of various points depending upon which mode was selected in step 204, as will be explained hereafter.

Referring now to the operation of the water quality monitor 100, step 202 of the process outlined in FIG. 4 is performed by pressing the power button 108. According to one embodiment, when the power button is pressed for less than three seconds (normal start), the system turns on and performs a self check, then waits for the user to select mode and sensitivity. When the power button is pressed for more than three seconds (fast start), the system turns on, performs a self check, and begins operation based on the most recent mode and sensitivity settings provided. If the power button is pressed for less than three seconds while the system is running, a back light behind the display panel lights up temporarily (e.g., seven seconds), then goes out. If the power button is pressed for more than three seconds while the system is running, the system shuts down.

In step 204, the user selects a mode of operation by pressing the mode button 110. Repeatedly pressing the mode button 110 cycles through the available modes of operation, which are displayed on the display panel 114 as the modes are selected. According to one embodiment, there are three modes of operation: absolute measurement (mode I), relative measurement (mode II), and slope measurement (Mode III). When the absolute measurement mode (mode I) is selected in step 204, the user selects a maximum acceptable value of total dissolved solids in step 206, beyond which the system will signal an overvalue. The system is provided with a default value, such as, for example, 400 parts-per-million (ppm), but the user has the option to change this value.

For example, in one embodiment, the user can select values ranging between 10 and 1500 ppm. The value is selected by repeatedly pressing the set button 112 of the monitor device 100. The selected values cycle to progressively lower threshold values, in increments of 10 ppm at values below, for example, 100 ppm, i.e., 90, 80, 70, down to the minimum value, then cycling to the maximum value and continuing down from the maximum value in increments of 100 ppm at higher values, i.e., 1500, 1400, 1300, etc. The selected values are shown in the display panel as the user cycles through. When no change is made for a selected period, i.e., seven seconds, for example, the displayed value is set as the reference value.

When mode I is selected in step 204, the reference value selected in step 206 is used in the comparison step 220, and the system skips step 210. When TDS, as reflected by the average value obtained in step 214, exceeds the selected reference value, the process proceeds to step 224 where the overvalue signal is produced. If the overvalue signal was in response to a temporary spike in TDS, after which the TDS level dropped below the threshold value, the system will return to normal operation when the reset button is pressed. However, if the signal was due to an overall rise in TDS, the user will need to change the selected sensitivity setting at 206 to prevent the system from repeatedly producing an overvalue signal. This is reflected in FIG. 4, in which the Mode I path is shown returning from the reset step (228) to the select sensitivity step 206.

If mode II, relative measurement mode, is selected in step 204, the system uses, as a threshold value, a number that is established relative to a measured value. When the system is reset or powered up, the system provides a default multiplier, such as, for example 2.50, though the user can change the multiplier in step 206. In one embodiment this is accomplished by repeatedly pressing the set button 112 until the desired multiplier is displayed in the display panel.

In one embodiment, the user can select multiplier values of between 1.10 and 4.00, in increments of 0.10. Additionally, the increments may be spaced further apart at the upper end. Once a multiplier value is selected, the system proceeds to step 208, and begins obtaining readings, and moves to step 210, where a reference value is set. To set the reference value, the system obtains a number of consecutive reading, such as, for example, thirty readings obtained at one second intervals. An average value of these readings is then derived and that value is multiplied by the multiplier selected in step 206. The resulting figure is saved as the reference value for the comparison step 220. The system then continues operation as previously described. If an overvalue is detected (224), the overvalue signal is produced (228) until the system is reset or powered down. When the system is reset, a new reference value is obtained—as shown by the mode II path from the reset step (228)—and operation proceeds, with a new reference value.

If mode III, slope measurement mode, is selected at step 204, the system operates according to mode I (absolute measurement), except that the system is also sensitive to sudden changes of TDS, even if the maximum TDS does not exceed the selected mode I threshold. For example, if the user selects mode III, the system operates under the most recent settings established under mode I, but the system also holds each derived value Y (214) for a selected period of time such as, for example, 30 seconds, and, in addition to comparing the newest value Y with the threshold value (220), it also compares the newest value Y with a value Y saved 30 seconds previously. If a difference between the two derived values exceeds a selected mode III threshold, the overvalue signal is produced.

Thus, if, for example, the selected mode III threshold is 120, the mode I threshold value is 400 ppm, and the previously saved value Y is 100 ppm, the system will signal an overvalue if the new derived value Y is greater than 220 ppm, indicating that TDS has increased more than 120 ppm over thirty seconds. On the other hand, a more gradual rise will not trigger the overvalue signal until the level reaches 400 ppm, at which time the system will respond as described with reference to mode I operation. The system provides a default mode III threshold value, but the user may change the default multiplier at step 206 as described with reference to modes I and II. The mode and sensitivity settings can be set at any time during operation of the system.

According to another embodiment of the invention, the system is configured to operate under modes I, II, and III simultaneously, such that an overvalue signal is produced if any of three thresholds are exceeded. The device includes default values for each threshold, which a user can change as described above.

Combinations of color and blink patterns of the status light 119 may be used to signal various conditions of operation. For example, a steady green light indicates normal operation of the device, while a steady red light indicates an overvalue signal. Flashing red may be used to indicate a power failure and operation on back-up battery power. These and other conditions may also be indicated in the display panel.

The term average, as used in the specification and claims, is intended to refer to any process of data manipulation to extract a single value from a number of different readings. This value may be derived by any appropriate method, including, for example, calculation by arithmetic mean, median, or mode. Furthermore, circuitry, such as integrating or differentiating circuits, for example, may be employed to produce similar results without calculation.

In step 208, the readings may be obtained continuously or at any convenient interval, such as one second as described, or more or less frequently. For example, readings may be obtained at intervals of ten seconds, one minute, or many minutes. The selection of the interval length is a design choice that will be dictated, in part, on factors such as the volume of water flowing in the water line, whether flow is continuous or intermittent, etc. Additionally, in the case of a constant reading, i.e., a constant current between the device electrodes, circuitry or software of the device may be configured to obtain the necessary information from the continuous flow of data.

Although the system is described as obtaining regularly spaced readings, and operating continuously, according to some embodiments, the system reads TDS at spaced intervals, of for example, once every five or ten minutes. According to another embodiment, the system does not operate at regularly spaced intervals or continuously, but in response to specific criteria. For example, the system may include a sensor configured to detect water flow, and to operate only while water is moving in the waterline. This prevents the system from sampling the same water repeatedly while downstream faucets are closed. According to another embodiment, the system operates at a rate that is proportionate to the rate of flow of water in the line, such that, while there is no flow, the system takes no readings, and as flow increases, the sample rate increases proportionately. This may provide more accurate data regarding overall quality of water in the line.

By correlating five readings to arrive at a TDS value, false alarms are minimized. For example, it is not uncommon for a fleck of metal or rust to separate from an inside wall of a water line and travel with the water down the line. Such a particle would induce a brief spike in the conductivity reading as it passed between the electrodes of the device. Obtaining an average of a plurality of readings helps to prevent such a spike from provoking an overvalue signal. It will be recognized that the number of readings that are averaged to obtain the TDS value is a design choice, and is not limited to the five readings described in the disclosed embodiments.

The electronic components of the system may include a memory in which software is stored for controlling operation of the device. Alternatively, the system may employ electronic components such as logic circuits for control of the device and registers for storing data. Operations of the system may be integrated into a single semiconductor device, or may be controlled by a number of discrete circuits or chips. The circuitry of the device may be maintained in a single device body, or may be distributed among several components. Furthermore, portions of the system operation may be controlled by an appropriately programmed processing unit separate from the system, such as, for example, a personal computer linked to the system. Thus, according to one embodiment, a user may program the operational parameters of the system by selecting and entering desired settings at a computer terminal, then uploading the instructions to the monitoring device via a wireless communication link, for example. The device may also include a backup battery for continued operation while no power is available. These and other alternative configurations are within the ability of one of ordinary skill in the art, and fall within the scope of the invention.

Furthermore, while the functions of embodiments of the invention may be described or claimed with reference to discrete circuits, such references are to be construed as including equivalent configurations, including those outlined above. Thus, for example, claims that recite two or more individual circuits, each configured to perform specified tasks, are to be construed as also reading on devices in which the recited tasks are performed by a single combined circuit, as well as on devices in which some or all of the tasks are performed by more generalized devices such as programmable logic systems and computers.

A partial list of water contaminants that can be detected by conductivity testing as described with reference to the principles of the invention includes substances such as aluminum, calcium, chloride, chromium, copper, iron, lead, magnesium, manganese, nitrate nitrogen, sodium, sulfate, and zinc. This list includes many of the most common and most harmful contaminants.

Embodiments of the invention have been described with reference to devices and methods that employ conductivity testing to establish TDS. According to alternate embodiments, characteristics of a water sample other than conductivity may also be employed to test the overall suitability of the water for a selected use. For example, an embodiment of the invention provides a device for monitoring turbidity of water, which otherwise operates in a manner similar to other embodiments described herein.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. In particular, the summary and abstract are intended to provide brief outlines of embodiments of the invention, and are not to be considered complete or limiting with respect to any aspect of the invention. The invention is not limited except as by the appended claims.

The invention claimed is:

1. A method for monitoring water quality in a water line using conduction characteristics, comprising:
   obtaining a first plurality of water sample characteristics from water in the water line;
   averaging the first plurality of water sample characteristics;
   deriving a first water quality value from the average of the first plurality of water sample characteristics;
   outputting a first signal corresponding to the first water quality value;
   obtaining an additional water sample characteristic from water in the line;
   replacing an oldest one of the first plurality of water sample characteristic with the additional water sample characteristic, forming thereby a second plurality of water sample characteristics;
   averaging the second plurality of water sample characteristics;
   deriving a second water quality value from the average of the second plurality of water sample characteristics;
   comparing the second water quality value with a threshold value; and
   outputting a second signal corresponding to the second water quality value.

2. The method of claim 1 wherein:
   the step of obtaining a first plurality of water sample characteristics comprises, for each of the water sample characteristics obtained, passing a current between a pair of electrodes positioned in the water line, and obtaining a value of conductivity of water in the water line from a level of the current; and
   the step of averaging the first plurality of water quality values comprises averaging the respective conductivity values.

3. The method of claim 1 wherein each of the water quality values of the first and second pluralities of water quality values is expressed as parts per million of total dissolved solids in the water.

4. The method of claim 1 wherein the step of obtaining a first plurality of water sample characteristics comprises obtaining water sample characteristics at intervals of about one second.

5. The method of claim 1, further comprising:
   outputting an overvalue signal if the second water quality value exceeds the threshold value.

6. The method of claim 1 wherein the step of deriving a second water quality value from the average of the second plurality of water sample characteristics comprises:
   deriving an average of the second plurality of water sample characteristics; and
   obtaining a difference between the average of the second plurality of water sample characteristics and an average of a previously obtained plurality of water sample characteristics;
   the method further comprising outputting an ivervalue signal if the difference exceeds the threshold difference.

7. The method of claim 1, further comprising:
   uploading operational parameters from a separate processing unit to a device configured to perform the obtaining and deriving steps.

8. The method of claim 1, further comprising:
   storing data associated with the first and second water quality values in a memory.

9. The method of claim 8, further comprising:
   compiling the stored data and tracking water quality value in the water line over time.

10. The method of claim 1 wherein the step of obtaining a first plurality of water sample characteristics comprises obtaining water sample characteristics at a rate corresponding to a volume of water flowing in the line.

11. The method of claim 1 wherein the step of obtaining a second plurality of water sample characteristics from water in the water line comprises obtaining each of the plurality of water sample characteristics while the water is in the water line.

12. The method of claim 1 wherein the steps of obtaining first and second pluralities of water sample characteristics from water in a water line each comprise obtaining the respective plurality of water sample characteristics from water in a water line of a residence.

13. The method of claim 12, further comprising:
transmitting data associated with the first and second water quality values to a central collection facility;
collecting and compiling data from a plurality of residences at the central collection facility; and
compiling the collected data and tracking water quality value over time and by region.

14. A method of monitoring water quality in a water line, comprising:
obtaining a first plurality of water sample characteristics from water in the line;
deriving a first water quality value based on an average of the first plurality of water sample characteristics;
outputting a first signal corresponding to the first water quality value;
obtaining a second plurality of water sample characteristics from water in the line, the second plurality including at least one of the first plurality of water sample characteristics;
deriving a second water quality value based on an average of the second plurality of water sample characteristics;
outputting a second signal corresponding to the second water quality value;
comparing the second signal with a reference value; and
outputting an overvalue signal if the second signal exceeds the reference value.

15. The method of claim 14 wherein the step of obtaining the second plurality of water sample characteristics comprises obtaining an additional water sample characteristic, and replacing one of the first plurality of water sample characteristics with the additional water sample characteristic.

16. The method of claim 14, comprising obtaining a continuous stream of water sample characteristics at regular intervals, and wherein teh first and second pluarlities of water sample characteristics are each obtained from the continuous stream of water sample characteristics.

17. The method of claim 14. further comprising comparing a difference between the first quality value and a previously derived water quality value with a threshold value and outputting an overvalue signal if the difference exceeds the threshold value.

18. The method of claim 17 wherein the threshold value represents a selected maximum acceptable rate of change of water quality.

19. The method of claim 18 wherein the maximum acceptable rate of change is one of a rate of change of water quality over time or a rate of change of water quality over volume of water through the water line.

20. The method of claim 14 wherein the obtaining steps comprise repeatedly measuring a level of conductivity of water in the water line, and wherein each of the water sample characteristics of the first and second pluralities of water sample characteristics is a figure that corresponds to a level of conductivity of water in the water line at a moment the respective measurement is made.

21. The method of claim 20 wherein the repeatedly measuring step comprises passing an electric current between a pair of probes positioned in the water line.

22. he method of claim 14 wherein the obtaining steps comprise repeatedly measuring a level of turbidity of water in the water line, and wherein each of the first and second pluralities of water sample characteristics is a figure that corresponds to a level of turbidity of water in the water line at a moment that respective measurement is made.

23. The method of claim 14, comprising storing each of the first and second pluralities of water sample characteristics in a memory.

24. The method of claim 14, comprising storing each of the first and second water quality values as a datum in a memory.

25. The method of claim 24 wherein the storing step comprises transmitting each of the first and second water quality values to a central data collection facility.

26. The method of claim 14 wherein the outputting steps comprise displaying, on a screen, a value corresponding to the water quality value.

27. The method of claim 14 wherein the overvalue signal comprises an audible alarm.

28. The method of claim 14 wherein the overvalue signal comprises a visible signal.

29. The method of claim 14, further comprising closing a water valve in response to the overvalue signal.

30. The method of claim 14, further comprising obtaining a benchmark water quality value, and deriving the reference value from the benchmark value.

31. The method of claim 30, wherein the step of deriving the reference value comprises selecting a multiplier value and deriving the reference value by multiplying the benchmark water quality value by the selected multiplier value.

32. The method of claim 30 wherein the step of obtaining a benchmark water quality value comprises deriving the benchmark water quality value from a plurality of water sample characteristics obtained prior to obtaining the first plurality of water sample characteristics.

33. The method of claim 2, further comprising transmitting operating parameters to a device configured to perform the obtaining, deriving, outputting, and comparing steps.

* * * * *

UNITED STATES PATENT AND TRADEMARK OFFICE
CERTIFICATE OF CORRECTION

| | |
|---|---|
| PATENT NO. | : 7,505,857 B2 |
| APPLICATION NO. | : 11/466378 |
| DATED | : March 17, 2009 |
| INVENTOR(S) | : Jason W. Howell et al. |

It is certified that error appears in the above-identified patent and that said Letters Patent is hereby corrected as shown below:

In the Claims:

<u>Column 10</u>
Line 56, "ivervalue" should read --overvalue--.

<u>Column 11</u>
Line 49, "teh" should read --the--.

<u>Column 12</u>
Line 18, "he" should read --The--.

Signed and Sealed this
Seventeenth Day of September, 2013

Teresa Stanek Rea
*Deputy Director of the United States Patent and Trademark Office*